United States Patent
Ekdahl et al.

(10) Patent No.: US 6,212,948 B1
(45) Date of Patent: Apr. 10, 2001

(54) APPARATUS AND METHOD TO OBTAIN REPRESENTATIVE SAMPLES OF OIL WELL PRODUCTION

(76) Inventors: Donald W. Ekdahl, 3031 21st St., Bakersfield, CA (US) 93301; Donald C. Nelson, 4408 Onix Ct., Bakersfield, CA (US) 93308

( * ) Notice: Subject to any disclaimer, the term of this patent is extended or adjusted under 35 U.S.C. 154(b) by 0 days.

(21) Appl. No.: 09/340,517

(22) Filed: Jun. 28, 1999

(51) Int. Cl.[7] ............ G01N 25/18; E21B 49/08; G01F 13/00
(52) U.S. Cl. ............ 73/152.18; 73/152.31; 73/61.41; 73/64.44; 73/64.56; 166/250.16; 166/264
(58) Field of Search ............ 73/152.18, 152.29, 73/152.31, 152.52, 53.04, 61.41, 861.04, 61.44, 64.55, 64.56, 19.05; 166/250.15, 250.16, 264, 250.01

(56) References Cited

U.S. PATENT DOCUMENTS

| | | | |
|---|---|---|---|
| 3,130,808 | * 4/1964 | Walker, Jr. et al. | 181/0.5 |
| 3,660,644 | * 5/1972 | Hammond et al. | 235/92 PL |
| 4,015,194 | * 3/1977 | Epling | 324/1 |
| 4,813,270 | * 3/1989 | Baillie | 73/61 R |
| 4,901,563 | * 2/1990 | Pearson | 73/151 |
| 5,209,765 | * 5/1993 | Kolpak et al. | 55/168 |
| 5,211,842 | * 5/1993 | Tuss et al. | 210/87 |
| 5,283,001 | * 2/1994 | Gregoli et al. | 252/314 |
| 5,612,493 | * 3/1997 | Alexander | 73/152.55 |
| 5,633,470 | * 5/1997 | Song | 73/861.04 |
| 5,654,502 | * 8/1997 | Dutton | 73/152.18 |
| 5,865,247 | * 2/1999 | Patterson et al. | 166/252.1 |

* cited by examiner

Primary Examiner—Hezron Williams
Assistant Examiner—David J. Wiggins
(74) Attorney, Agent, or Firm—Donald D. Mon

(57) ABSTRACT

An apparatus and process for obtaining representative samples of fluids produced from one or more oil wells by means of a closed vessel chamber with lease water supply port connected to a lease water supply line, where a pressure sensor within such internal chamber is used together with a flowmeter and liquid-sensing probe or oil/water interface sensor employed in the fluid flow path lines to determine a rate of well production along with absolute or relative amounts of oil, water and gas contents. A complex and extensive distribution of fluid flowpath lines and flow control valves are employed in this well tester to achieve a multitude of process steps such as chamber filling with well fluids, chamber gas expulsion, chamber pressure measurement, chamber contents settling and stratification, gas compression, gas purging, lease water injection, chamber oil expulsion, line flushing of well fluids, air/oil interface sensing, gas/oil interface sensing, fluid flow measurement, time interval measurement and gas volume calculation via Boyle's Law by choosing a proper setting of selectable valve arrangements among a well selector valve, gas control valve, test fluid inlet valve, by-pass valve, lease water valve, purge valve and sample exit line selector valve.

5 Claims, 11 Drawing Sheets

APPARATUS AND METHOD TO OBTAIN REPRESENTATIVE SAMPLES OF OIL WELL PRODUCTION

FIELD OF THE INVENTION

Apparatus and method for obtaining representative samples of the fluids produced by an oil well, and measuring the amounts of oil, water and gas in the sample.

BACKGROUND OF THE INVENTION

The need for accurate and timely oil well production data is critical. The extremely erosive and harsh environments in which well pumping systems operate create constant deterioration of the equipment, often resulting in rapid failure. To maintain production rates in the face of this situation, well operators invest substantial resources in well maintenance. For wells using steam drives and waterfloods well servicing is frequently the highest non-energy cost.

Knowledge of the production performance of an individual well on a current basis is the most important tool for maximizing production from the well and optimizing reservoir management. Because of the well-known advantages of prompt, accurate and low-cost performance data, numerous testing systems have been devised. Despite extensive previous efforts, there still remain many unsolved disadvantages, resulting in uncertainly of accuracy of the data, and long testing periods because the sampling procedures were very slow themselves.

Early pioneers in production of oil from wells as early as about 1900 began to measure the performance of their individual wells. The early efforts were little more than collecting well production for a day or so, and measuring the gross output and the relative amounts of water and oil with a dip stick or tape measure. That method is still widely used, but is not truly sufficient when optimum and most economical production is the objective.

Open tank systems can indeed accurately measure the output of low production rate wells, but they take a very long time to collect the sample. Worse, production conditions can vary widely during that long period. A true production sample representative of a short preselected period of time can not be obtained with this practice.

Beginning in the 1960's this procedure was improved by providing tall, vertical, closed separators and using various mechanical devices to measure the levels and read them out. These largely succeeded because of the advent of pollution control rules, which adversely affected the earlier open tank samplers rather than because of any inherent sampling superiority. The closed samplers simply produced less pollution.

Beginning in the 1980's improved sensing devices became available, and their use improved the accuracy of the procedures but still their collection times were slow, and they did not provide for suitable purging between tests, leading to contaminated samples. Also the potential for measurement errors in low flow rate wells was and is much higher than it should be. Additional problems reside in the complexity and inaccuracies of the more modern sensors and measuring devices, especially at slow flow rates. Because of their sophistication, the initial costs and the costs of maintenance and operation of these newer systems are much higher than they should be.

Especially in periods of low oil prices at the well, it is essential not only to minimize operation and maintenance costs, but also to maximize production both of the well and of its field. Dollars are very scarce in times of low oil prices, and any reduction of costs is not only welcomed but may contribute to the decision to keep a well or field in operation rather than to shut it down.

It is an object of this invention to provide sampling apparatus and method that can obtain a sample which is suitably small to reflect fluid produced in a relatively short time, even from low production rate wells. A single sampler has the capability to service a substantial number of wells, often up to 60 wells, and to provide frequent samples from them. Importantly, the lines leading to it are fully purged of fluid remaining from previous tests as is the apparatus itself so that the sample is truly representative of well production at a very specific time.

This apparatus can be automated to perform its method on a programmed basis without supervision, and can also be programmed to alert the owner to any departure of a well's performance from previous samplings, thereby alerting the operator to potential problems in a particular well.

BRIEF DESCRIPTION OF THE INVENTION

Sampling apparatus according to this invention includes a vessel having a bottom wall, a top wall and a vertically extending sidewall which form a sample chamber.

A water inlet passes through the bottom wall. A test fluid exit port passes through the top wall. A test fluid line opens into the vessel and a mid-elevation. A test fluid inlet valve controls flow from a test fluid supply line to the test fluid line. A purge line opens into the vessel at a lower elevation.

A sample exit sensor senses flow from the sample exit port, and a purge control valve controls flow from the purge line.

A return line returns fluid from the vessel to a point of use. A flow line interconnects the purge line and the sample exit line at their intersection downstream from their respective valves. A selector valve is placed between said intersection and the fluid exit valve.

A gas discharge line is connected between said fluid exit line and said return line. A gas control valve is placed in the gas discharge line.

A flow meter device is placed in said return line.

A test fluid by-pass line interconnects the test fluid supply line to the return line. A by pass valve selectively controls flow through the test fluid inlet line and through the return line.

By suitable manipulation of the aforesaid valves along with the availability of lease water under pressure, test fluid under well pressure, and a suitable return to the system, a unique sampling process can be accomplished.

This system utilizes water from a separate water supply often called "lease water". This water is used and discarded as part of the procedure. This is not water from the samples.

A procedure according to this invention begins with the vessel full of water. First, the contents of the lines leading to the vessel wherever they may have come from will be forced into the vessel for a measured period of time. The pressure is that of the well production fluid. The water expelled by this incoming fluid passes through the flow meter. From this is calculated how long a time it will take for the flow from this well to completely form a suitable sample, or how large the sample will be in a selected period of time. This places produced material in the chamber.

The vessel next is closed and its contents permitted to settle (gas on top, water on the bottom, oil in between). During this time, test fluid from the well continues to purge the supply line through the by-pass.

Next gas is measured and purged. The lease water drives the fluids upwardly until liquid is sensed at sensor 56 (the supply line purge continuing). The gases are compressed to the lease water pressure. The pressure is released and the flow through the flow meter enables the amount of gas to be calculated.

Oil is next purged from the tank by further supply of lease water thereby driving oil out through the exit port. This driving action will continue until water has been sensed at the sensor for a given length of time, usually one minute. Thus, all of the piping downstream of the vessel will be purged.

Now a production sample is collected by opening the sample inlet valve and the water exit valve. The sample fluid will drive the purge water from the vessel and occupy the vessel by a known amount. After that time the vessel is closed and the sample water, gas and oil separate.

Thereafter using lease water pressure, the gas is compressed. Then the compressed gas is permitted to expand so that its amount can be calculated.

Then the gas is purged, and lease water is admitted to drive the oil through the flow meter to calculate its volume, and the system is open to flush purge the system.

The above and other features of this invention will be fully understood from the following detailed description and the accompanying drawings, in which:

DETAILED DESCRIPTION OF THE INVENTION

Figure 1:
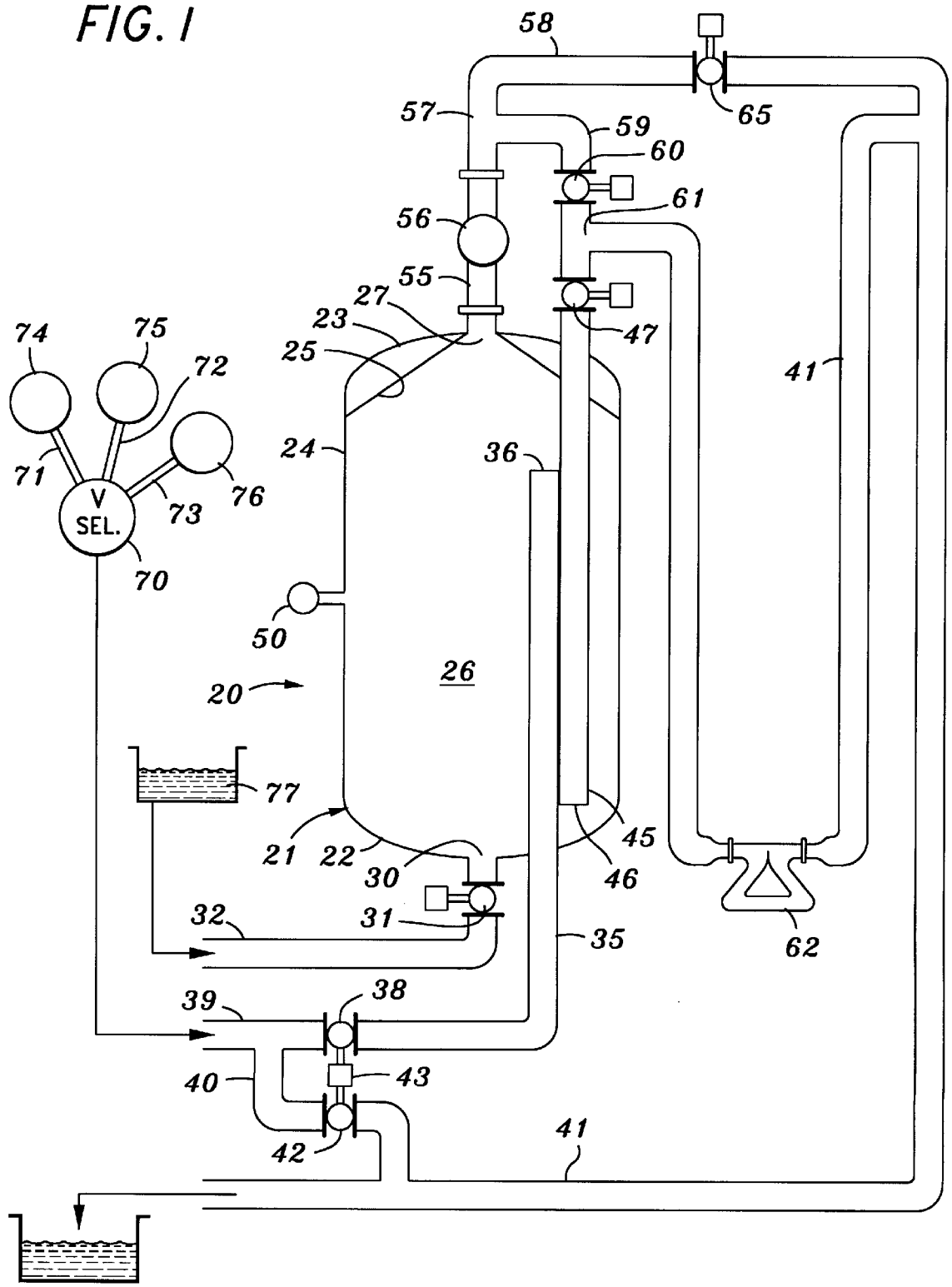
FIG. 1 shows the presently-preferred embodiment of a tester in its repose condition, coupled to a group of producing wells, shown principally in schematic notation.

A well tester 20 is shown in FIG. 1. It includes a vessel 21 which has a bottom wall 22, a top vessel wall 23 and a peripheral sidewall 24. It is a closed vessel with a substantial vertical dimension compared to its diameter. A frusto-conical chamber top wall 25 reduces the cross-section of sample chamber 26, and connects to an exit port 27 through the vessel top wall.

A water supply port 30 enters the sample chamber through the bottom wall. A water valve 31 is placed in a water line 32 which interconnects a supply 77 of lease water to the water supply port.

A test fluid line 35 enters the vessel, most conveniently through bottom 22. Its discharge end 36 is at a mid-elevation in the sample chamber. It could instead enter through the side wall, but the disclosed arrangement is much more convenient.

A test fluid inlet valve 38 interconnects the test fluid line 35 to sampling line 39. A by-pass line 40 interconnects a return line 41 and the sampling line 39. A by-pass valve 42 is disposed in the by-pass line. It will ordinarily be activated by an actuator 43 which sets valves 38 and 42 in alternate flow conditions.

A purge line 45 extends from an inlet opening 46 near the bottom of the chamber, out of the chamber, conveniently through the top wall. A purge valve 47 is placed in purge line 45.

A pressure transducer 50 or other pressure measurement device senses the pressure inside the chamber.

An exit line 55 exists from the exit port 27. A liquid sensing probe 56 in the exit line will detect the interface or presence of a liquid, so it is sensitive to a gas/liquid interface or of a water/liquid interface when one passes the probe.

Exit line 55 branches at intersection 57 to a gas discharge line 58 and to a sample exit line 59. A selector valve 60 in line 59 is upstream of an intersection 61 of the sample exit line 59, return line 41, and purge line 45. A flow meter 62 measures the rate of flow of liquid through return line 41.

A gas control valve 65 in gas discharge line 58 controls flow through line 58 to return line 41.

As shown in FIG. 1, this tester is plumbed into a system which selectively provides flow from a selected well. A central station 70 is connected by collector line 71, 72, 73 to individual wells 74, 75, 76. This valve will select the well, and through line 39 will send product from it to the tester.

Lease water is supplied from a source 77. Return line 41 will return the output from the tester to a sump or some other receptacle or system, along with product fluid from other wells.

Later it will be appreciated that the sampled fluids are all returned to the production along with what lease water is used. Lease water is used and disposed of the same as any water in the sampled fluids.

Controls for this system will customarily be programmed, but could instead be manually operated. The details of an automatic control are not an essential part of this invention and may readily be devised by a person skilled in the controls art. Care must be taken in the lines where flow and pressure and measured, to be certain that the velocities are such as to prevent stratification and the collection of a sample in a suitably short time.

A testing cycle will begin with the tester entirely filled with lease water, except for a small amount of oil from the previous test in line 35 downstream from valve 38.

TEST LINE PURGE AND WELL FLOW RATE MEASUREMENT

Figure 2:
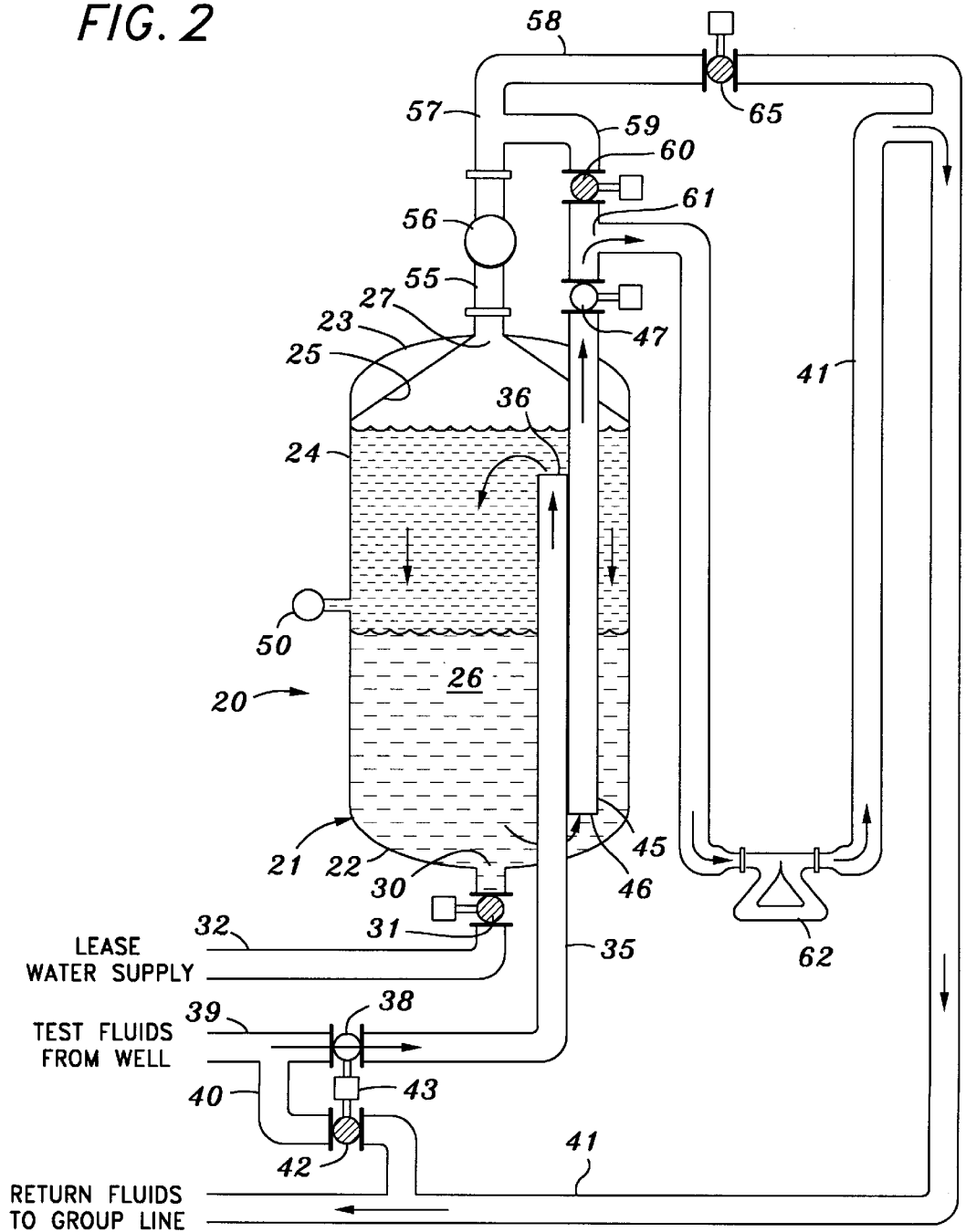
FIGS. 2–11 show the tester of FIG. 1 in an operating sequence, illustrating the valve settings and flow patterns in the various method steps.

The first step is to purge the entire line from the central station to the tester. This step passes oil from a previous test through the system, and serves the important function of measuring the flow rate of the well itself. For this purpose, the well's own production fluids force the previous oil ahead of it (FIG. 2). Valve 38 is open, valve 42 is closed, and fluid flows through line 35 into chamber 26. Valves 31 and 50 are closed. Valve 47 is open.

This will pass flow from the chamber through flow meter 62 and out return line 41. This flow will be continued for a measured period of time, usually about three minutes. Because the volume of the lines from the central station to the tester is known, it can be calculated how long this flow must be continued in order fully to purge the supply line to the tester and the tester itself. Accordingly, it is continued for that period of time.

Figure 3:
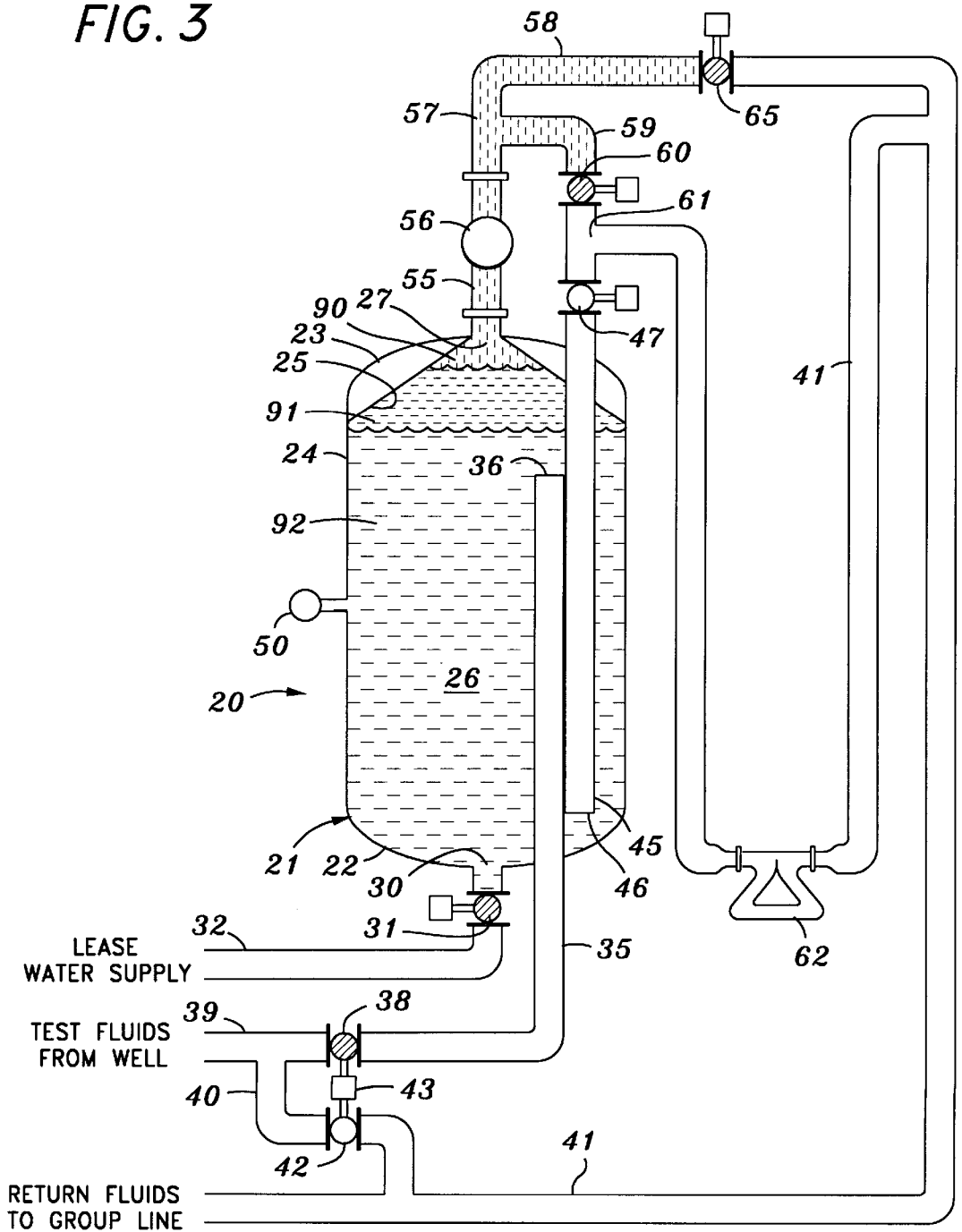

Now these fluids must be removed. Valves 31, 38, 60 and 65 are closed (FIG. 3). Valve 42 is open and by-passes well fluids to the return line. For about three minutes the fluids in the vessel are permitted to settle. The gas 90 and oil 91 rise above the water 92. The test line continues to be purged.

Figure 4:
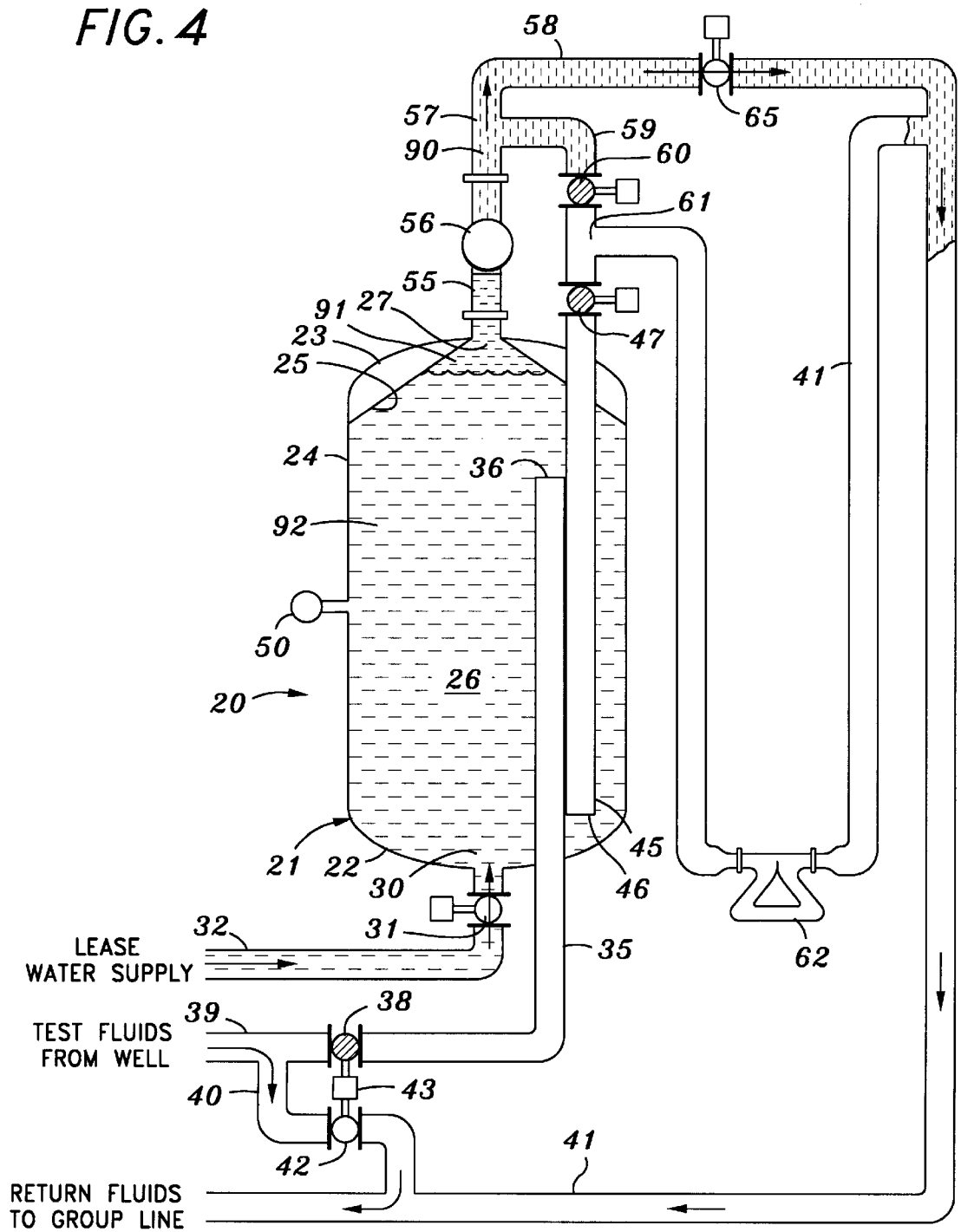
Figure 5:
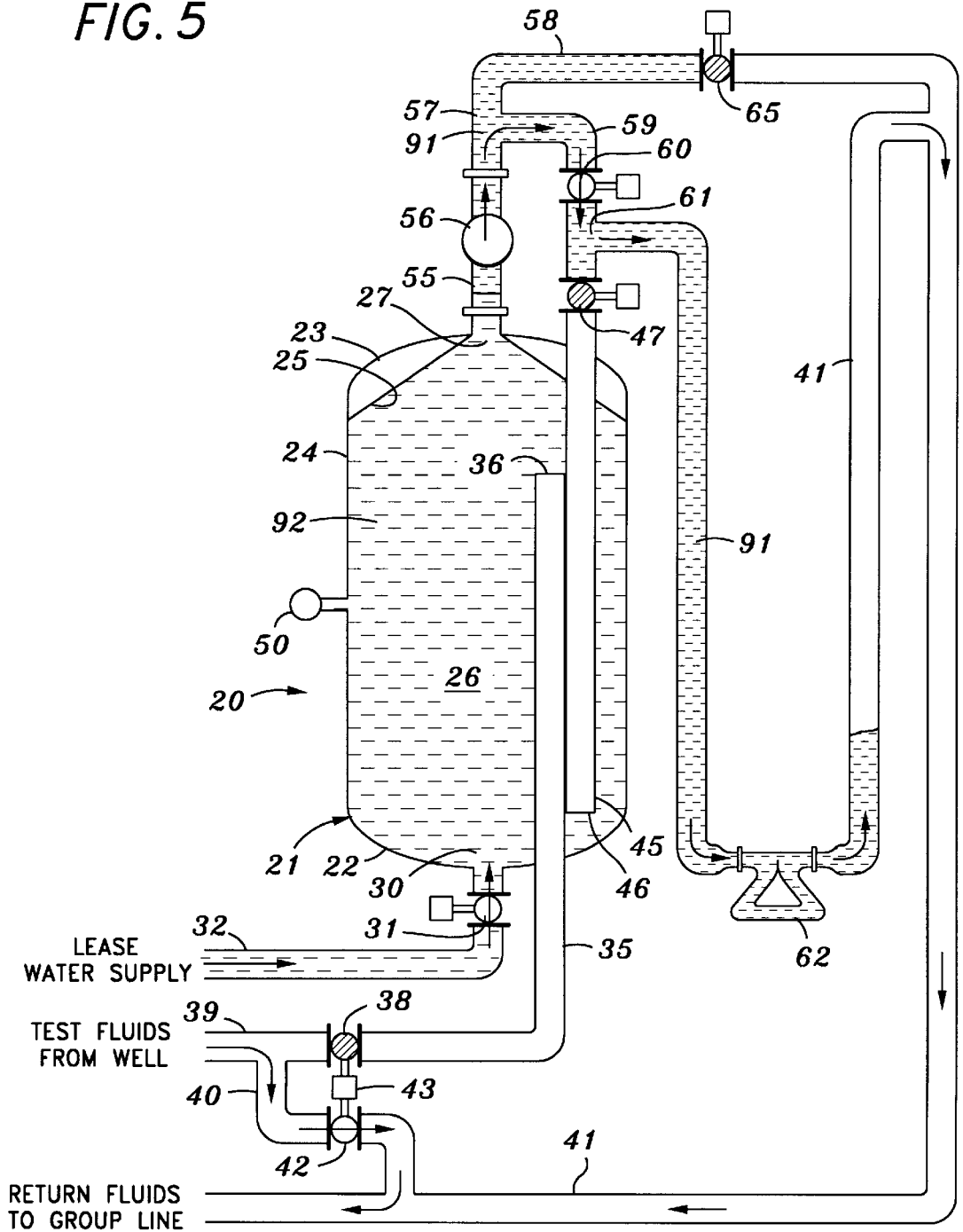

Next, (FIG. 4) lease water valve 31 and gas valve 65 will be opened so gas will be driven out until liquid (oil) is sensed by sensor 56. Then (FIG. 5), oil 91 will be removed by closing gas valve 65, valve 47, and valve 38. The lease water will drive the oil ahead of it, and out through return line 41. This will continue until water is sensed at probe 56. These conditions will persist for perhaps 60 seconds, during which lines 59 and 41 are fully purged. Notice that this vessel is now filled with lease water.

Test Fill

Figure 6:
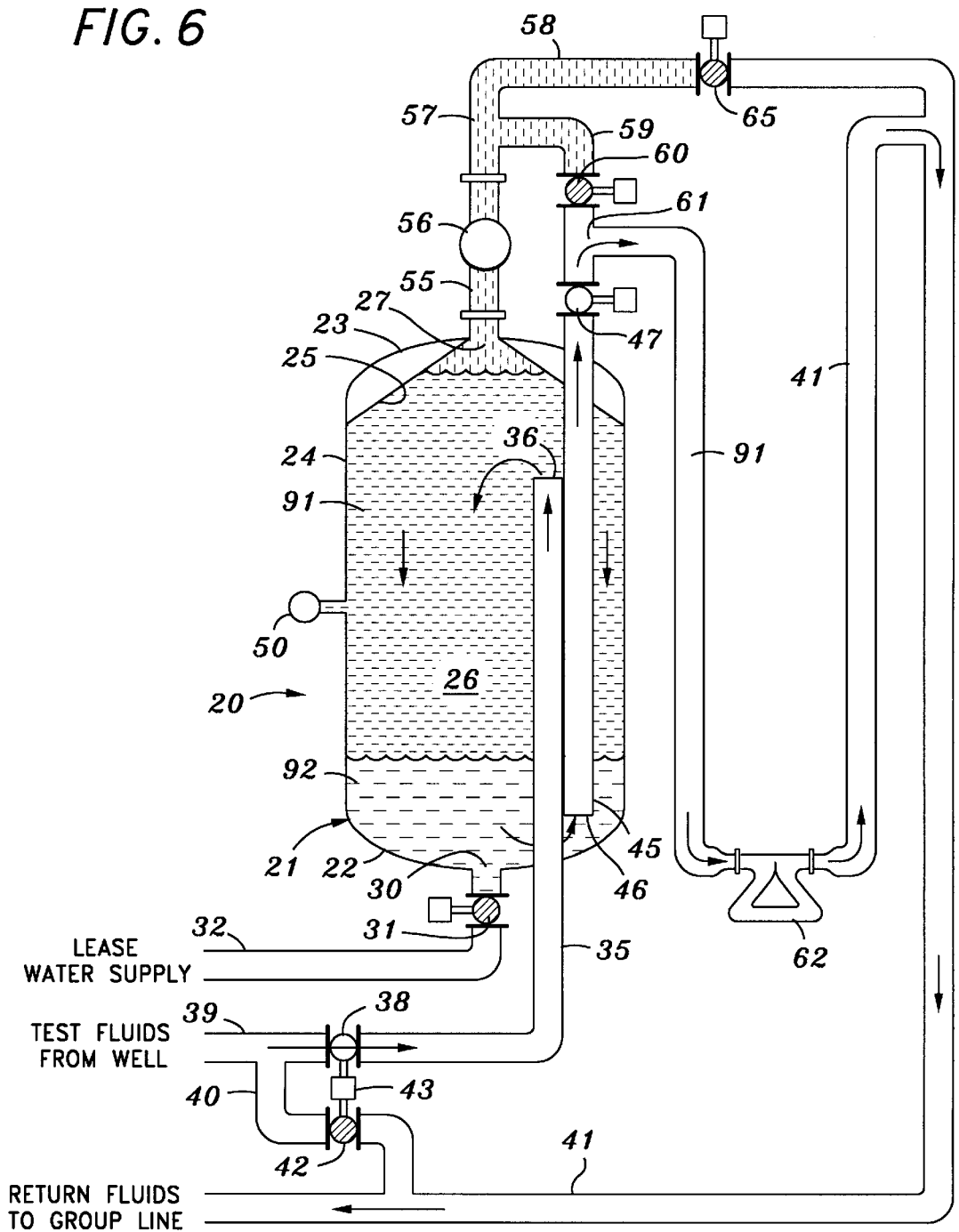

With valves 31, 65, 47 and 42 closed, valve 38 is opened to admit a sample of well fluids to be tested from line 39, which now contains only fluids from the well being tested (FIG. 6). The well fluids will displace lease water out of the vessel through line 45, past valve 47, and out through return line 41. The gross flow volume is calculated from the flow meter as a function of flow rate and time. This gives the well's flow rate. It will also give the amount of well fluid injected into the vessel.

Settle Step

Figure 7:
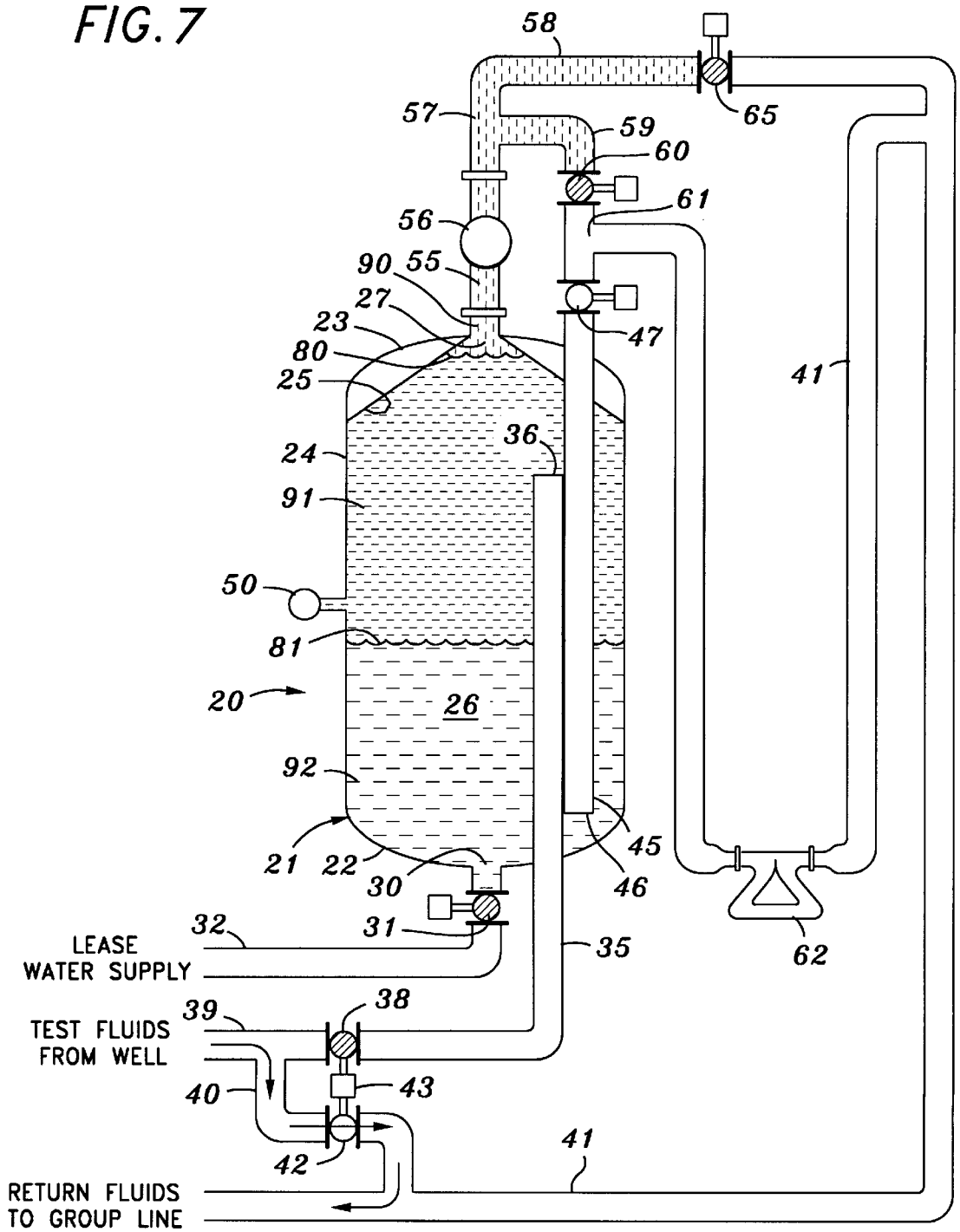

All valves except by-pass valve 42 are closed (FIG. 7). Well fluids are by-passed to the return line, and the contents of the chamber are permitted to settle, i.e. for the gas, oil and water to stratify.

Interfaces 80 between gas and oil and 81 between oil and water are formed. The return line is filled with water. The volume of the sample is known, and the analysis can now be made.

Gas Measurement and Gas Purge

Figure 8:
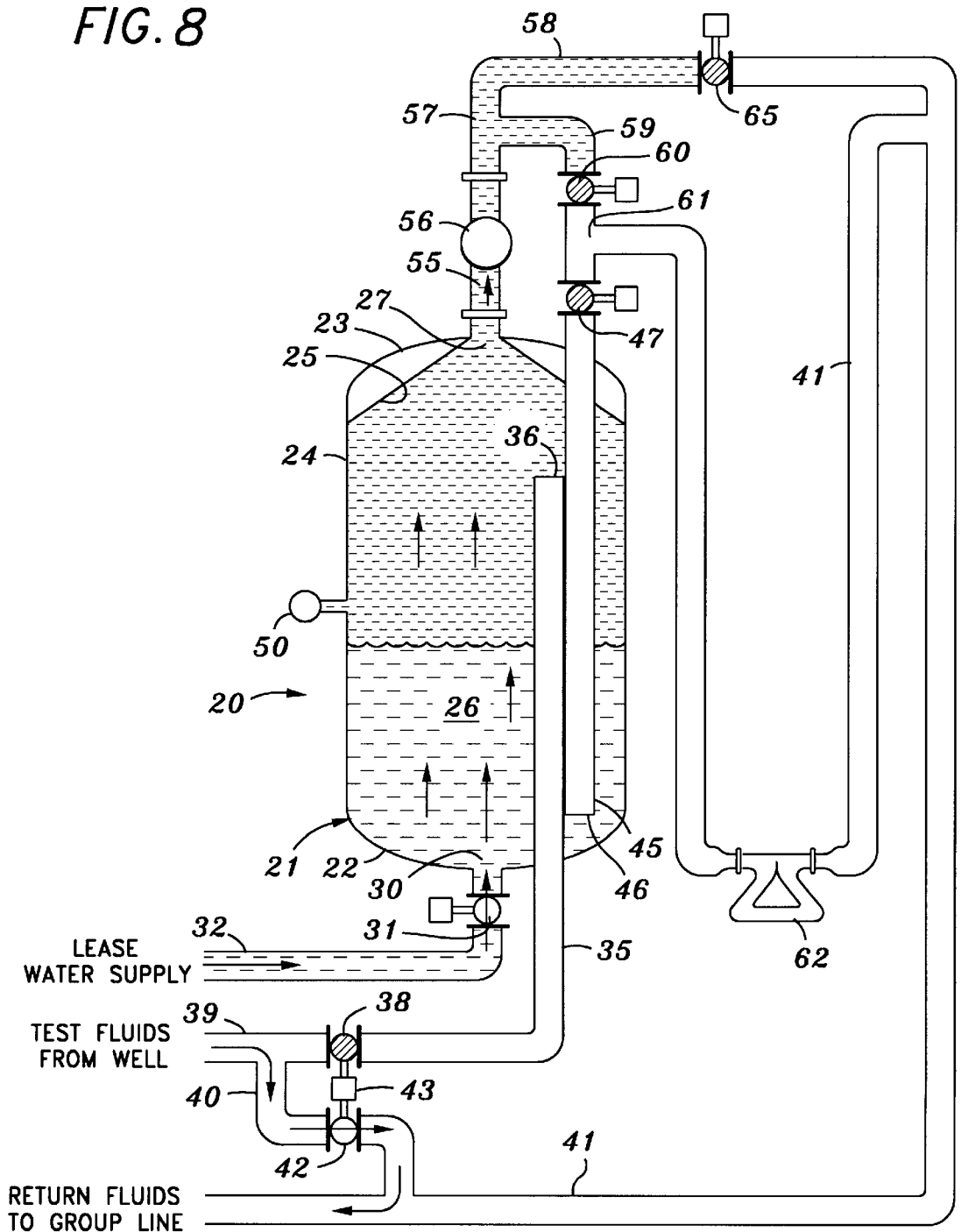

Valves 65, 60, 47 and 38 are all closed (FIG. 8). Valve 31 is opened to admit lease water under lease water pressure. Once this is stabilized, the pressure at sensor 50 is read. This is P1 for use in the Boyle's Law equation.

Figure 9:
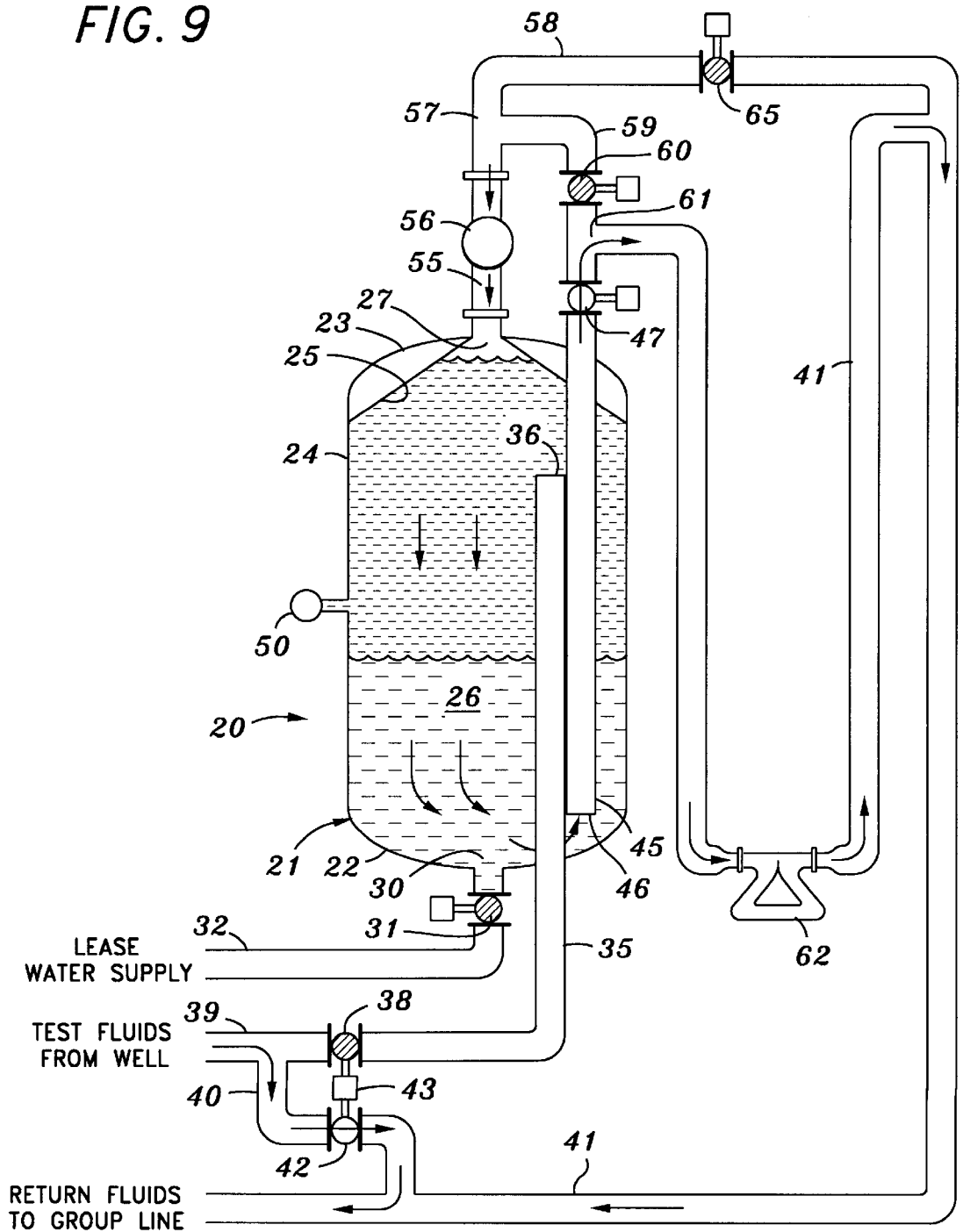

Next, (FIG. 9) valve 47 is opened, which reduces vessel pressure to that of the return line. This pressure is read by sensor 50. This is P2 in the Boyle's Law equation. The amount of water which passed through flow meter 62 during the expansion is the expanded volume of the gas. If necessary, the amount of vessel volume change when the pressure is released can be included in the calculation of that volume. P1V1=P2V2 is the classical Boyle's Law formula, which yields the compressed volume under well pressure.

Figure 10:
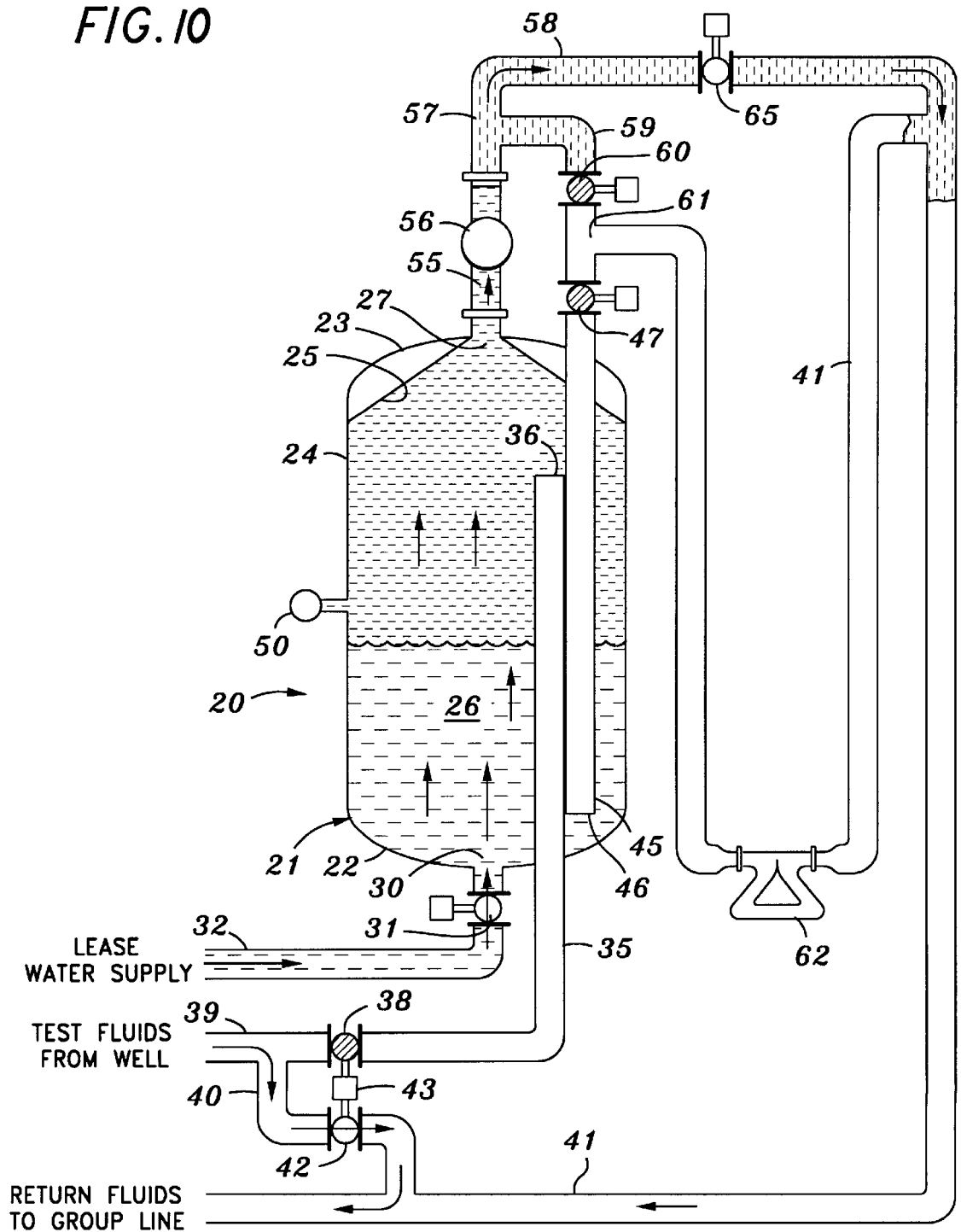

Gas is purged (FIG. 10) from the system by opening gas valve 65 and lease water valve 31. When liquid is sensed at probe 56, the vessel will be known to be free from the gas.

Oil Measurement

Figure 11:
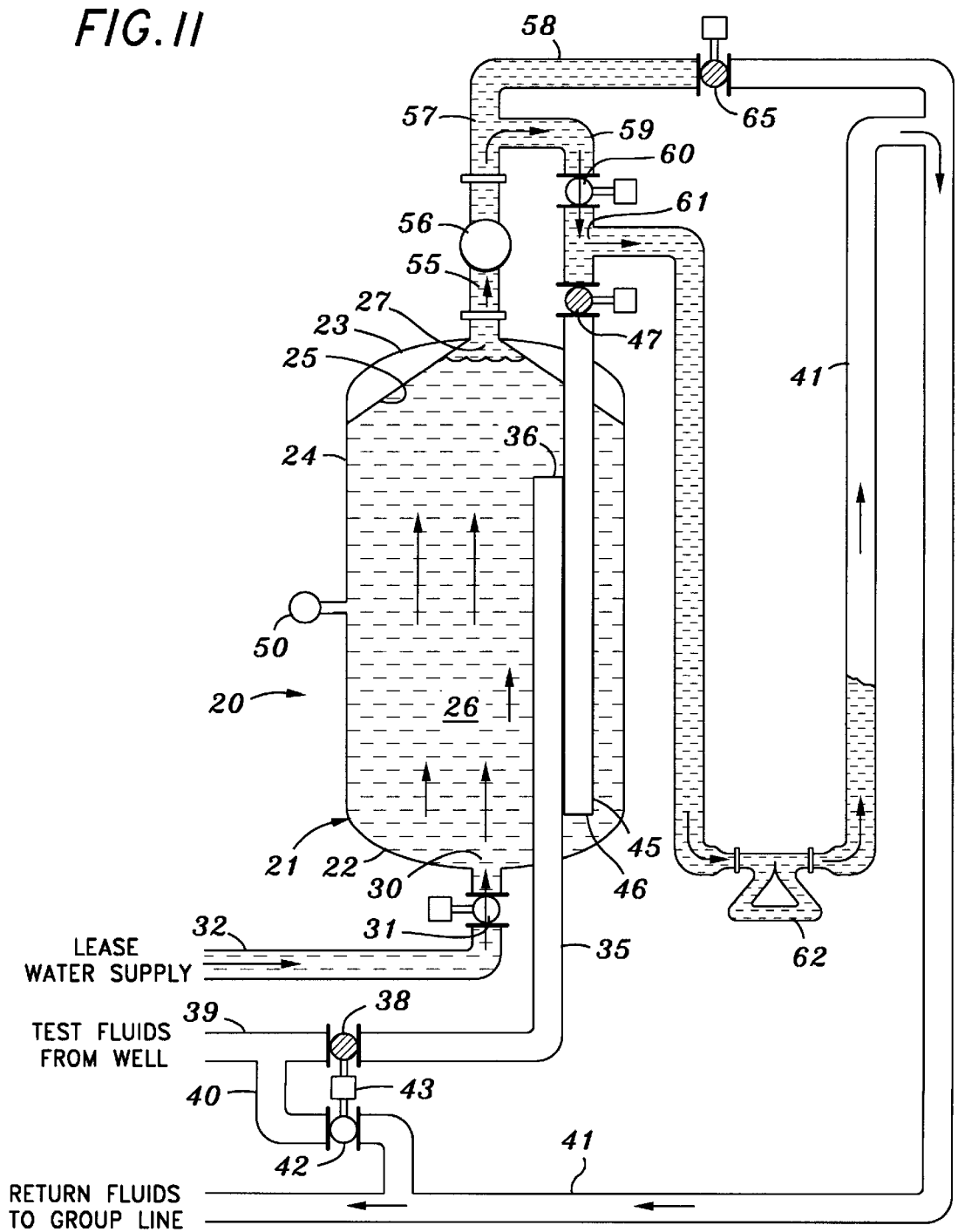

Valves 65, 47, and 38 are closed (FIG. 11). Lease water will drive oil through lines 55, 59 and 41. When sensor 56 detects water, a volume of fluid equal to the sample oil volume will have flowed through the flow meter. This is the measurement of oil.

Then this flow is continued for a predetermined length of time to flush all downstream piping. About 60 seconds will usually suffice, but it depends on the dimensional parameters of the system.

During these measurement steps, by-pass valve 42 will be open to by-pass well fluid that are not in the measuring loop.

The system is now full of lease water, fully purged and ready for the next sampling from another well as described above.

This is an elegantly simple construction which enables a very sophisticated sampling procedure. Short and frequent runs are available and reliable. The system can be programmed to recognize significant changes in the performance of a well, and can be made to function without substantial supervision.

The flow meter and probes are selected for their property of signaling the arrival of an interface, and the valves are simple off-on types whose actuators (shown as squares in the drawings) can be actuated by relays controlled from a central location.

The method itself is unique in its property to present a nearly completely clean receptacle and system for assay purposes. Its energy requirements are minimal. For its operation it does require a supply of "lease" water under a known pressure. However the vessel itself usually contains only about 60 gallons for successful testing (although it can be larger), so that the amount of water which must be supported and discarded is rather small. Furthermore, in most installations it can be re-used.

This invention is not to be limited by the embodiments shown in the drawings and described in the description, which are given by way of example and not of limitation, but only in accordance with the scope of the appended claims.

What is claimed is:

1. A well tester for obtaining and assaying a production sample of test fluids from an oil well to learn its production rate, and content of gas if any, oil and water, said tester comprising:

a closed vessel having an internal chamber with a lease water supply port, an exit port, and a purge port;

a lease water supply line connected to said lease water inlet port and a lease water valve in said lease water line selectively to open or to close said lease water line to flow of fluid;

a test fluid line entering said chamber with a discharge end at a mid-elevation therein, a test fluid inlet valve in said test fluid line selectively to open or to close said test fluid line to flow of fluid;

a sampling line receiving test fluid from a source connected to said test fluid inlet valve;

a return line to return fluids;

a by-pass line interconnecting said test fluid line upstream from said test fluid inlet valve to said return line;

a by-pass valve in said by-pass line selectively to open or to close said by-pass line to flow of fluid;

a purge line through said vessel having an inlet end near the bottom of the vessel;

a purge valve in said purge line selectively to open or to close said purge line to flow of fluid;

a pressure sensor in said chamber to measure pressure therein;

an exit line connected to said exit port;

a liquid-sensing probe adapted to sense a gas/oil and an oil/water interface, disposed in said exit line;

a gas discharge line branching from said exit line;

a gas control valve in said gas discharge line selectively to open or to close said gas discharge line to flow of fluid;

a sample exit line branching from said exit line;

a selector valve in said sample exit line selectively to open or to close to fluid flow;

said return line being joined to said sample exit line between said purge valve and said selector valve;

a flow meter to measure rate or volume of fluid flow in said return line;

said return line connecting to said gas discharge line downstream from said gas control valve;

whereby with selected settings of said valves, the tester and the supply lines leading to it may be substantially purged of prior samples, the rate of well production determined, the volume of sample obtained in a given time known, and the absolute and relative amounts of oil and water, and gas if present, may be learned.

2. Apparatus according to claim 1 in which a frusto-conical top wall in said chamber narrows to said exit port, said chamber having a substantial vertical dimension.

3. Apparatus according to claim 1 in which said test fluid line enters said chamber, extends upwardly into said chamber, and said purge line extends downwardly into said chamber, the outlet end of the test fluid line being at a higher elevation than the entry end of the purge line.

4. A system for testing the production of a plurality of wells, one at a time, comprising:
 a well selector valve adapted to receive production fluid individually from a plurality of wells, and to select any of said wells, one at a time, to provide fluids from a selected well; and
 a well tester according to claim 1 in which said test fluid line receives fluid from said well selector valve; and
 a source of lease water under pressure connected to said lease water supply line.

5. A process for obtaining and assaying a production sample from an oil well utilizing a well tester having a closed vessel forming an internal chamber with a lease water inlet line from a source of leased water under pressure entering said chamber; a test fluid line from a source of production fluid entering said chamber and discharging at a mid-elevation therein; a purge line exiting said chamber from a lower elevation therein; an exit port at the top of said chamber; a sensor in said exit line responsive to gas/oil and oil/water interfaces; a return line; a gas discharge line branching from said exit line; said return line branching from said exit line; a flow valve in said return line; a lease water valve in said lease water supply line; a gas control valve in said gas discharge line; a purge valve in said purge line; a selector valve in said exit line; said return line joining said exit line between said selection valve and said purge valve; a flow meter in said return line; a test fluid inlet valve in said test fluid line; a by-pass line between said test fluid inlet valve and said return line; and a by-pass valve in said by-pass line;

said process comprising the following steps in the order recited;

a. with the chamber full of water, opening the test fluid inlet valve, closing the by-pass valve, opening the purge valve and closing the selector valve and gas control valve, and forcing well fluid into said chamber and through the flow meter for a measured period of time, thereby to learn the time required to purge lines leading to the chamber of well fluids from other wells;

b. then closing the test fluid inlet valve, opening the by-pass valve, closing the gas control valve and opening the purge valve, thereby permitting the contents of the chamber to settle, while well fluids flow through the by-pass line;

c. then opening the gas control valve, closing the purge valve, and opening the lease water valve, injecting lease water into the chamber to expel gas until the interface sensor senses the presence of an air/oil interface;

d. then opening the selector valve and closing the gas control valve, injecting lease water into the chamber until water is sensed by the sensor, and continuing for a period of time sufficient to purge the system of previous content, using lease water;

e. then closing the lease water valve by-pass valve and selector valve, and supplying well tester fluids to said chamber while measuring the rate or volume of lease water passing through the flow meter as a measure of well fluids injected into the chamber during a selected period of time;

f. then closing the gas control valve, lease water valve, test fluid inlet valve, and selector valve and opening the by-pass valve, permitting the oil, water, and gas if present to settle and stratify;

g. then closing the purge valve and opening the lease water valve, injecting lease water into the chamber to compress any gas present, and measuring the chamber pressure at that time;

h. closing the lease water valve and opening the purge valve, thereby permitting chamber pressure, and measuring the resulting chamber pressure and fluid flow through the flow meter to determine by Boyle's law the volume of gas in the sample;

i. opening the gas control valve and lease water valve, and closing the test fluid inlet valve and purge valve, and purging gas from the vessel until a gas/oil interface is sensed by the sensor;

j. closing the gas control valve and opening the selector valve, forcing oil from the chamber until an oil/water interface is sensed by the probe, then also opening said gas control valve and continuing the supply of lease water for a period of time to flush the gas line and return line beyond the flow meter, and measuring the volume of oil by calculating the time of flow before the oil/water interface was sensed.

\* \* \* \* \*